(12) United States Patent
Tajnaföi

(10) Patent No.: US 6,448,067 B1
(45) Date of Patent: Sep. 10, 2002

(54) METHOD FOR DETERMINING THE GLUCOSE CONTENT OF A BLOOD SAMPLE

(75) Inventor: Gábor Tajnaföi, Budapest (HU)

(73) Assignee: 77 Elektronika Muszeripari KFT, Budapest (HU)

( * ) Notice: Subject to any disclaimer, the term of this patent is extended or adjusted under 35 U.S.C. 154(b) by 0 days.

(21) Appl. No.: 09/540,713

(22) Filed: Mar. 31, 2000

Related U.S. Application Data

(63) Continuation of application No. PCT/HU98/00091, filed on Oct. 2, 1998.

(30) Foreign Application Priority Data

Oct. 3, 1997 (HU) ............................................. P9701607

(51) Int. Cl.$^7$ ............................. G01N 21/47; C12M 1/34
(52) U.S. Cl. ................................. 435/288.7; 435/287.9; 422/82.05; 356/39; 356/448
(58) Field of Search ........................... 435/286.1, 288.7, 435/287.9, 805; 422/55–58, 82.05, 82.06; 436/66, 67, 164, 805; 356/445, 448, 39; 600/365–367

(56) References Cited

U.S. PATENT DOCUMENTS

| | | | |
|---|---|---|---|
| 4,199,261 A | 4/1980 | Tidd et al. | |
| 4,935,346 A | 6/1990 | Phillips et al. | |
| 4,985,205 A | 1/1991 | Fritsche et al. | ............... 422/56 |
| 5,049,487 A | 9/1991 | Phillips et al. | |
| 5,051,901 A | 9/1991 | Endo | ............... 364/413.11 |
| 5,059,394 A | 10/1991 | Phillips et al. | |
| 5,179,005 A | 1/1993 | Phillips et al. | |
| 5,246,858 A | 9/1993 | Arbuckle et al. | ............... 436/8 |
| 5,350,676 A | 9/1994 | Oberhardt et al. | ............... 435/13 |
| 5,567,869 A | 10/1996 | Hauch et al. | ............... 73/64.41 |
| 6,069,011 A | * 5/2000 | Riedel | |

FOREIGN PATENT DOCUMENTS

| | | | |
|---|---|---|---|
| WO | WO92/01065 | 1/1992 | ............ G12Q/1/56 |
| WO | WO92/15988 | 9/1992 | ........... G10N/21/00 |
| WO | WO 99/18426 A1 | * 4/1999 | |

* cited by examiner

Primary Examiner—William H. Beisner
(74) Attorney, Agent, or Firm—McDonnell Boehnen Hulbert & Berghoff

(57) ABSTRACT

The invention relates to a method and apparatus for determining a chemical component from a sample, where the sample is measured on a test strip with the help of a color reaction. The method concerns finding the measurement time $T_m$ for measuring the reflection of the test strip. The method comprises the following steps: a) Recording the R(t) function, b) Determining the $T_0$ starting time at the detection of the wetting through of the sample, c) Generating the function $R(t)+L(t)$, d) Monitoring and storing the ext[$R(t)+L(t)$] extreme value of the $R(t)+L(t)$ function, and, at the same time, e) Generating the function $R(t)+L(t)-\text{ext}[R(t)+L(t)]$ from the time of reaching an ext[$R(t)+L(t)$] extreme value, f) when the $R(t)+L(t)-\text{ext}[R(t)+L(t)]$ function reaches a predetermined $C(t)$ value, determining the $T_m$ measuring time.

25 Claims, 9 Drawing Sheets

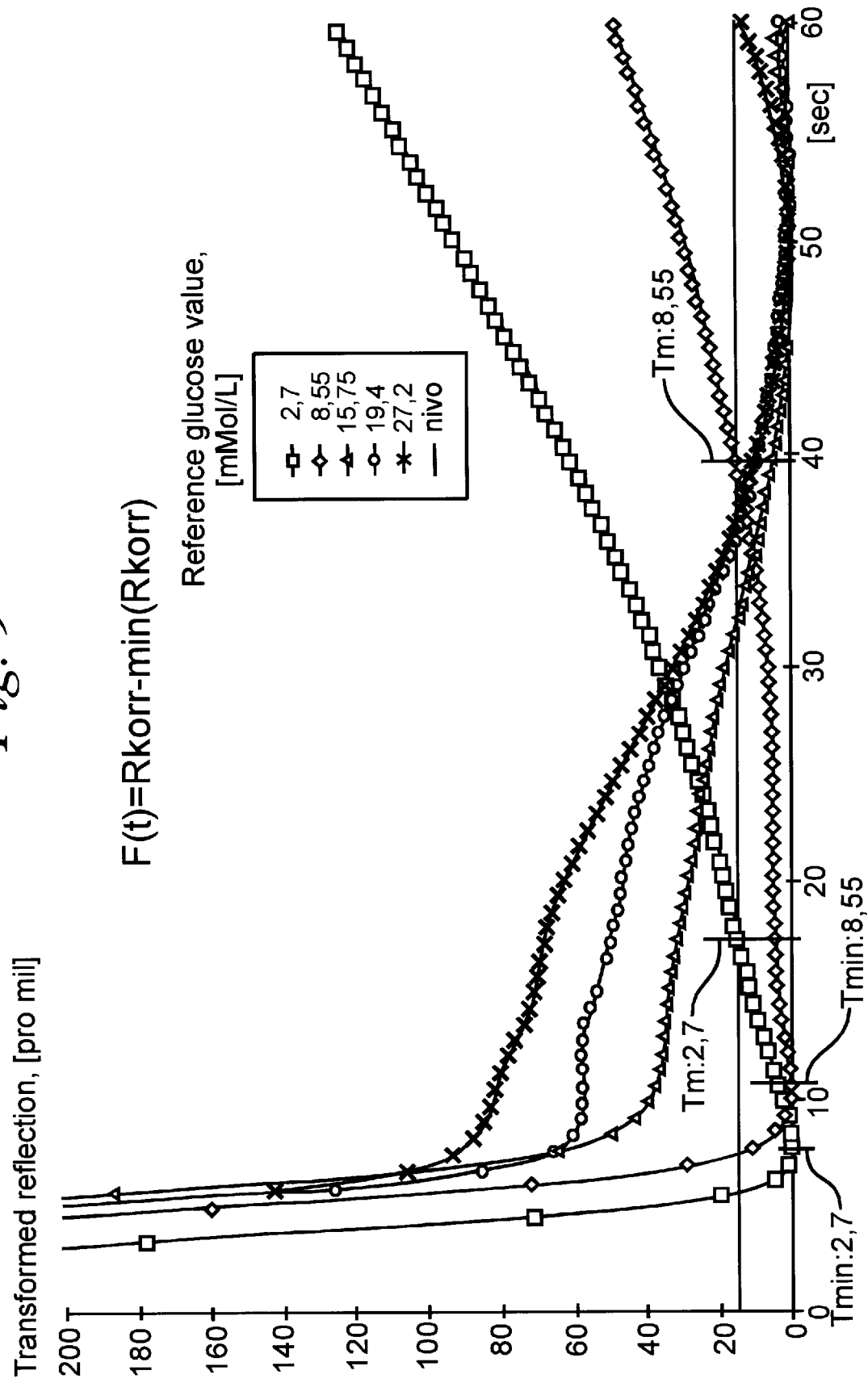

METHOD FOR DETERMINING THE GLUCOSE CONTENT OF A BLOOD SAMPLE

The application is a continuation of International Application PCT/HU98/00091, with an international filing date of Oct. 2, 1998.

FIELD OF THE PRESENT INVENTION

The present invention relates to a method and apparatus for determining a chemical component from a sample of matter, in particular for determining the glucose content of blood from a blood sample.

BACKGROUND OF THE PRESENT INVENTION

It is generally known that diabetics are treating themselves in daily life. This is made possible by the use of domestic blood glucose measurement. In the known methods, patients with diabetes place a drop of blood on a test strip, which contains the reagent. The reagent will react with the glucose content of the blood, and generates a well-defined color. The reaction is a multi-stage reaction and is commonly known. The glucose-oxidase enzyme creates hydrogen-peroxide ($H_2O_2$) from the glucose content of the blood, the oxygen of the air and of the water present in the blood. The amount of the $H_2O_2$ generated is proportional to the amount of the glucose, and a peroxidase enzyme further activates it. The activated $H_2O_2$ oxidizes the indicator (also commonly known) in the test strip, which will change its color. This change of color may be accurately measured.

Earlier test strips have been washed or wiped after the application of the sample, and the color has been determined by comparison with a color chart. More recently, the color has been determined by a small electronic reading device, which calculated automatically the glucose content of the blood sample. The modem test strips are of the so-called no-wipe type, i.e., the blood sample need not be wiped or washed off. With these no-wipe strips the detection of the color reaction is performed on the opposite side to where the sample has been placed. The test strip is provided with a reagent carrier, usually a textile or foil patch, and the test strip is provided with a hole, through which the opposite side of the reagent carrier may be observed. These test strips are almost exclusively analyzed by reading devices, which provide much more objective measurement than the subjective comparison with the color chart. During the reading, the previous devices have measured the reflection of the reagent carrier on a predetermined wavelength. The color generated by the color reaction in the reflection carrier, or more properly on the back side of the carrier, is deduced from the measured reflection value.

The color reaction on such test strips progresses relatively fast, and both at the start of the reaction and after the completion of the reaction, various effects can occur, which affect the results of the color reaction itself. Therefore, in order to determine precisely the result of the color reaction, it is important to perform the reflection measurement serving as the basis of the glucose measurement in a well-defined time interval. Only in this manner is it possible to calibrate properly the relation between the color and the sugar content of the sample.

With the first known devices the measurements were done in the following manner: The patient switched on the device or switched from the stand-by state into the measuring state, after having positioned the sample. This method was not adequate, because the delays until the measurement actually started were varying, due to the switching on, even with by same person. Therefore the need arose to develop such methods, which ensured that the interval between placing the sample on the test strip and the start of the measurements could be determined uniformly, so that the precision of the measurements could improve. Therefore it is desirable to detect automatically, with the measurement device, the start of the color reaction and to detect its shape, so that the device could automatically determine a following time interval when the reflection measurement should be performed. The reflection measurement made in this time interval then could serve as a basis for the determination of the glucose content. Alternatively, in the case of continuous or sampled measurement it is sought to determine when the time $T_m$ (time point) occurs, so that a single reflection value measured in this time point $T_m$ could be the basis of the determination of the glucose content. The general object of the present invention is to provide a method for determining this $T_m$ time point.

When determining this time point, several factors must be considered, which may present contradictory demands. Of course, it is of primary concern that the $T_m$ time point of the measurement should be determined in a reproducible manner, as well as the R reflection values measured in the $T_m$ time points so determined. The deduced blood glucose values should also be reproducible, i.e., the accuracy of the blood glucose measurements must not be worse than with known methods.

On the other hand, it is desirable to perform the measurement as quickly as possible, which is, firstly, convenient for the patient, and, secondly, so the battery in the measurement device may last longer. On the other hand, laboratory measurements have shown that the ideal time point for the measurement is dependent on the glucose content of the sample itself. With certain types of test strips it is advantageous to measure earlier the samples with lower glucose content, than those with a higher glucose content. The reason for this is that with some test strips the color reaction takes longer with higher glucose content. Conversely, there are test strips where the opposite is true, that is samples with higher glucose content should be measured earlier, because the color reaction is faster with the higher glucose content and the result is reached earlier. It is advisable to wait longer with low glucose samples until the end of the reaction or close to the end, in order to be able to determine the glucose content precisely. In other words, a good system must be capable of "recognizing", even before the final measurement, what the interval should be, and the measurement time $T_m$ can be adjusted accordingly.

This is achieved in newer devices by measuring quasi-continuously the reflection curve, and by determining dynamically the Final measurement time. This latter process contradicts the requirement for simple operations and calculations. This is an important aspect, because the blood glucose measurement devices should be small and portable (i.e., operating from battery), be simple to operate, and, last but not least, be cheap.

A continuous reflection measurement requires the continuous or frequent switching on/off of the light source, typically a LED, and inevitably have a high power consumption. Therefore, it is sought to substitute the continuous measurement with sampling on a frequency as low as possible. It may also be mentioned that a more complicated method requires a more sophisticated controlling processor, which is more expensive. On the other hand, a more complicated algorithm, in a given processor in a given time, allows the evaluation of fewer measurement points, which in turn will result in a less precise measurement. It is less significant, but may be taken into consideration that the power consumption of the processor is higher with more calculating steps. This latter factor may play a role if the controlling algorithm of the device is not made by digital processor but by analog circuits, e.g. due to considerations of reliability. With higher power consumption the device will operate for a shorter time, so indirectly its reliability will worsen (i.e. the probability of malfunction due to the run-down of the batteries will increase).

The document U.S. Pat. No. 4,199,261 (Tidd et al.) discloses an optical reflection meter, which is used to determine the glucose content in urine of diabetics. The device is capable of determining if the sample carrier is dry or wet, by comparing the measured reflection with a predetermined threshold value. The value measured on the dry sample carrier is used for calibrating the device. Following this, the user inserts the sample carrier, which has been wetted with the urine sample, in the device, which is automatically identified by the device. After this, the final measurement is made after a predetermined time interval following the recognition of the wet sample.

The documents U.S. Pat. Nos. 4,935,346 and 5,049,487 (Phillips et al) disclose a method similar to the previous method, but primarily for determining the sugar content of a blood sample. The device to perform the method is described in the document U.S. Pat. No. 5,059,394. This known method differs from the previous one in that placement of the blood sample—in practice, applying a drop of blood on the sample carrier, in this case a no-wipe test strip—causes the decrease of the reflection, which is detected immediately by the device. Thus the short, but uncertain time interval is excluded, which will necessarily arise in the previously described method of the document U.S. Pat. No. 4,199,261 (Tidd et al.), because of the delay between the wetting of the sample carrier with the urine and placing the sample carrier in the device.

In the method described in the document U.S. Pat. No. 4,935,346, the blood sample penetrates the sample carrier, which serves simultaneously as the reagent carrier, and the effective measurement is performed after a predetermined time, following the detection of the decrease in the reflection. This method effectively excludes the subjective elements of the measurement, but its disadvantage is that the measurement time is determined independently of the glucose content. It is a further disadvantage that it needs frequent samplings, to determine the exact time of wetting through of the sample, because the reflection curve is failing very steeply around the critical time. If sampling is made at longer intervals, the determination of the $T_0$ starting time will be less exact, and from there it follows that the time of the final measurement will also fluctuate in relation to the ideal measurement time determined by the calibration curve. E.g. with higher glucose contents, if the reaction is still in progress in the predetermined measurement time, the uncertainty of the measurement time will be reflected in the measured results.

This latter method has been improved by Phillips et al. according to a method disclosed in the document U.S. Pat. No. 5,179,005. In this known method, based on the theoretical background of the so-called Kubelka-Munk equations, which are well known in the art, the so-called K/S values are calculated, and the blood glucose content is determined on the basis of these K/S values. The final measurement time which serves as the basis of the calculations, is still determined using a predetermined time interval following an initial decrease in the reflection. A disadvantage of this known method is that it is still not able to consider the order of magnitude of the measured glucose content when determining the measurement time. Thus, the measurement is not always made at the ideal time, and further, there must be a trade-off between the accuracy of the measurement and the sampling frequency.

Therefore, it is an object of the present invention to provide a method, which allows the determination of the measurement time in a manner avoiding or at least minimizing the disadvantages of the known solutions. Further objectives of the present invention are to determine the measurement time with a simple algorithm, and to determine a measurement time, which is set at or near the ideal time, dependent on the glucose content to be measured. It is still a further object to provide a method where the sampling frequency may be kept relatively low, in order to keep the power consumption low. Because the light sources of the measurement devices are normally the largest energy users, this is an important factor. The blood glucose measurements are also negatively affected by temperature variations, hence it is preferable that the method of the invention should deliver results independent of the measurement temperature.

SUMMARY OF THE INVENTION

In the method according to the present invention, the sample to be measured is positioned on one side of a test strip containing a reagent causing a color reaction directly or through an intermediate reaction with the clinical component to be measured. The components of the sample penetrate the test strip and start the color reaction at the other side of the test strip. The content of the component in the sample—in particular the glucose content of the blood sample—is determined by measuring through optical reflection measurement the result of the color reaction, particularly the developing color or darkening, and by comparing with earlier calibrating measurements. In the following, by color reaction any clinical or physicochemical reaction is meant that causes any change in the sample that may be indicated or measured by an optical reflection measurement. That is, the expression "color reaction" also includes any chemical reaction, where there is no real change of color—the change of the spectrum of the reflected light—but only the measured intensity is changed, that is some darkening or lightening is detected. Obviously, the above effects may appear mixed.

The invention further relates to an apparatus for determining a chemical component from a sample of matter, in particular for determining the glucose content of a blood sample, particularly for implementing the method according to the invention. The apparatus of the invention includes a sample holder accommodating the test strip which contains the chemistry for the reaction. The apparatus further includes a light source for illuminating the reaction area of the test strip in the holder, such as a light emitting diode (LED), and a circuit for measuring the intensity of the light reflected from the sample, such as a photo-detector. The functioning of the apparatus is controlled by a programmable controller and analyzer circuit, such as a microprocessor, for processing the signals of the circuit for measuring the light intensity and for determining the chemical component, such as the glucose content of the blood sample.

According to the present invention, the above objectives are realized by a method, whereby the sample is positioned on one side of a test strip, which contains a reagent causing a color reaction, directly or through an intermediate reaction with the chemical component to be measured. The components of the sample penetrate the test strip and start the color reaction at the other side of the test strip. The content of the component in the sample, such as the glucose content of the blood sample, is determined by measuring through optical reflection measurement the result of the color reaction, such as the developing color or darkening, and by comparing it with earlier calibrating measurements. According to one embodiment of the present invention, the method includes illuminating the sample and measuring at discrete time intervals or substantially continuously the R reflection on the test strip and recording the R(t) function. The method also recites the detection of the wetting through of the sample, and determines the $T_0$ starting time, $T_0$, the starting time being not earlier than the time of detection of wetting through. The method then calls for generating from the $T_0$ starting time the function R(t)+L(t) where L(t) is a predetermined function, independent of the measured reflection, monitoring and storing the ext[R(t)+L(t)] extreme value of the R(t)+L(t) function—preferably its min[R(t)+L(t)] minimum value and, at the same time, generating the function R(t)+L(t)−ext[R(t)+L(t)] from the time of reaching at least one definite (true) ext[R(t)+L(t)] extreme value. When the R(t)+L(t)−ext[R(t)+L(t)] function reaches a predetermined C(t) value, the method calls for determining the $T_m$ measuring time, and determining from the R reflection value measured at the $T_m$ measuring time the content of the chemical component in the sample, preferably the glucose content of the blood sample.

The method according to the present invention is based on the recognition that the sudden reduction in reflection should not be the determining factor, but by utilizing the characteristic curve of the reaction being measured, that section must be found where the color reaction has already come to an end, but where the distorting effect of other phenomena has not yet affected or has only slightly affected the measurement result. We have discovered that at various glucose contents the color reaction progresses roughly at the same reaction rate. Though this color reaction does not fully separate in time from the wetting process, however, the manufacturers of test strips basically strive for this. They have already reached a point where, the sections with the maximum reaction rates of the characteristic reactions are separated. The color reaction involves a characteristic reaction rate, to which a predetermined slope of the reflection curve belongs. Therefore, the appropriate section of the reaction curve must be found which has a predetermined slope, and it can be conveniently found using the algorithm according to the invention. It will be apparent to one of ordinary skill in the art that the algorithm is easily programmable and that the results can be calculated with a simple, low-performance processor in just a few operational steps.

In certain cases, the L(t) value may be presented in tabular form and in this case the processor should perform only subtraction, addition and comparison, instead of division or multiplication. It can be recognized that the $T_o$ starting time need not be specified exactly, as the aim is merely to ensure that the method should not begin the generation of the $R_{corr}$=[R(t)+L(t)] value, or at least the search for the extreme value, until after the lapse of a predetermined period following the commencement of the wetting.

It is not necessary to determine the starting time of the wetting very precisely, since the method adjusts the final measurement to a time when the color reaction has already slowed down. That is, when the reflection curve changes more slowly, therefore, during the search for the minimum value the sampling frequency may be relatively low. However, attributable to the rather slow change in reflection, at the same time the exact determination of the final $T_m$ time is less critical than in the already known methods.

On the other hand, when the actual values are determined by interpolating the measured values, then the method according to the present invention may be applied advantageously for the so-called quick strips, where the reactions take place quickly. For example, the sampling frequency can be reduced so that the $T_m$ time point is made equal not to the n-th value $T_n$ in which $T_n$ time we would first observe the reaching of the C(t) function, but the exact value of $T_m$ can be a point of time determined by interpolating between the time $T_n$ and $T_{n-1}$, where $T_m$ is defined by the $F^*(T_m)$=C value. Here, the function $F^*(t)$ is the linear or higher order approximation of the function F(t)=R(t)+L(t)−ext[R(t)−L(t)] laid through points $T_{n-1}$, $F(T_{n-1})$ and $T_n$, $F(T_n)$. Of course, the measured reflection value $R_m$ can also be calculated from the reflection values $R(T_n)$ and $R(T_{n-1})$ by interpolation. The error caused by the interpolation will be very small because in this time interval the variation of R is quite low. A further benefit is that the procedure is less sensitive to the deviations caused by the fluctuation of the reaction rate, because it adjusts the measurement according to the variation in the reaction rate. Therefore, the aging of the test strips, the measurement temperature, vapor content and other factors affecting the reaction rate will but slightly deteriorate the accuracy of the glucose content measurement.

It is also known that the test strip manufacturers are characterizing the different production batches with a so-called code. A code number identifies the characteristics of the test strips of a batch. In order to comply with increasingly exact measurement methods, the manufacturers are using a steadily growing number of the codes. The method according to the invention allows for the adjustment to the fine differences in the characteristics of test strips having many code numbers.

In one exemplary embodiment of the method according to the present invention, L(t) is a linear function with a predetermined slope [L(t)=At+B, preferably L(t)=At and B=O], while C(t) is a constant function [C(t)=C]. However, it is also possible that L(t) is a second-order or a higher order function of time. C(t) can be specified, for example, in a more general polynomial form as well. Preferably, the wetting through of the sample is detected on the basis of a predetermined amount of change in reflection. This requires merely a comparison with a threshold value, therefore, its demand for processing power is rather modest. However, it may be more advantageous if the wetting through of the sample is detected by a predetermined rate of change in reflection. With this method it is possible to filter out the effects of, for example, the inadvertent moving of the sample and the reductions in reflection not involving a real reaction. Alternatively, the wetting of the sample may be detected on the basis of the reflection value reaching a predetermined limit value. This simplifies the programming of the processor, because in the starting phase it requires the storing of a single reflection value at one time.

In one particular preferred embodiment, a blood sample, full blood, blood plasma or serum is tested using the present invention. In practice it worked well if the illumination was made with an intensity of 0.01 to 1 mW and with a wavelength of 400 to 1500 nm. The intensity and the wavelength of the illumination must be chosen so that the illumination will not affect the progress of the color reaction through an eventual photochemical reaction.

As noted above, the invention further relates to an apparatus for determining a chemical component from a sample, in particular for determining the glucose content of a blood sample, particularly for implementing the method according to the invention. The apparatus is composed of a sample holder accommodating the test strip applied in the method and entering into chemical reaction with the sample. The apparatus is further composed of a light source for illuminating the sample placed into the sample holder, such as a light emitting diode (LED), a circuit for measuring the intensity of the light reflected from the sample, such as a photo-detector, and includes a programmable controller and analyzer circuit, such as a microprocessor for processing the signals of the circuit for measuring the light intensity and for determining the chemical component, such as the glucose content of the blood sample. According to this embodiment of the present invention, the programmable controller and analyzer circuit, such as microprocessor 13, is programmed for the execution of an embodiment of the method according to the present invention.

Another embodiment of the present invention further relates to a microprocessor readable storage medium with executable instructions of a program for a microprocessor for determining a chemical component from a sample, such as determining the glucose content of blood from a blood sample. The storage medium according to this embodiment of the present inventions stores instructions for performing the following steps:

a) measuring at discrete time intervals or substantially continuously the R reflection of the illuminated sample on the test strip and recording the R(t) function;
b) detecting the wetting through of the sample;
c) at the detection of the wetting through of the sample, determining the $T_0$ starting time, where $T_0$ starting time is not earlier than the time of detection of wetting through;
d) generating from $T_0$ starting time the function $R(t)+L(t)$ in which $L(t)$ is a predetermined function, independent of the measured reaction;
e) monitoring and storing the $ext[R(t)+L(t)]$ extreme value of the $R(t)+L(t)$ function, such as its minimum value $min[R(t)+L(t)]$;
f) generating the function $R(t)+L(t)-ext[R(t)+L(t)]$ from the time of reaching at least one definite (true) $ext[R(t)+L(t)]$ extreme value;
g) when the $R(t)+L(t)-ext[R(t)+L(t)]$ function reaches a predetermined $C(t)$ value, determining the $T_0$ measuring time; and
h) determining from the R reflection value measured at the $T_m$ measuring time the content of the chemical component in the sample, preferably the glucose content of the blood sample.

BRIEF DESCRIPTION OF DRAWINGS

The present invention is described in greater detail with reference to the accompanying drawings showing preferred embodiments of the present invention, where:

FIG. 9 is a graph that shows the transformed reflection curves of another type of test strip, calculated similarly to those of FIG. 6.

DETAILED DESCRIPTION OF THE PRESENT INVENTION

Figure 1:
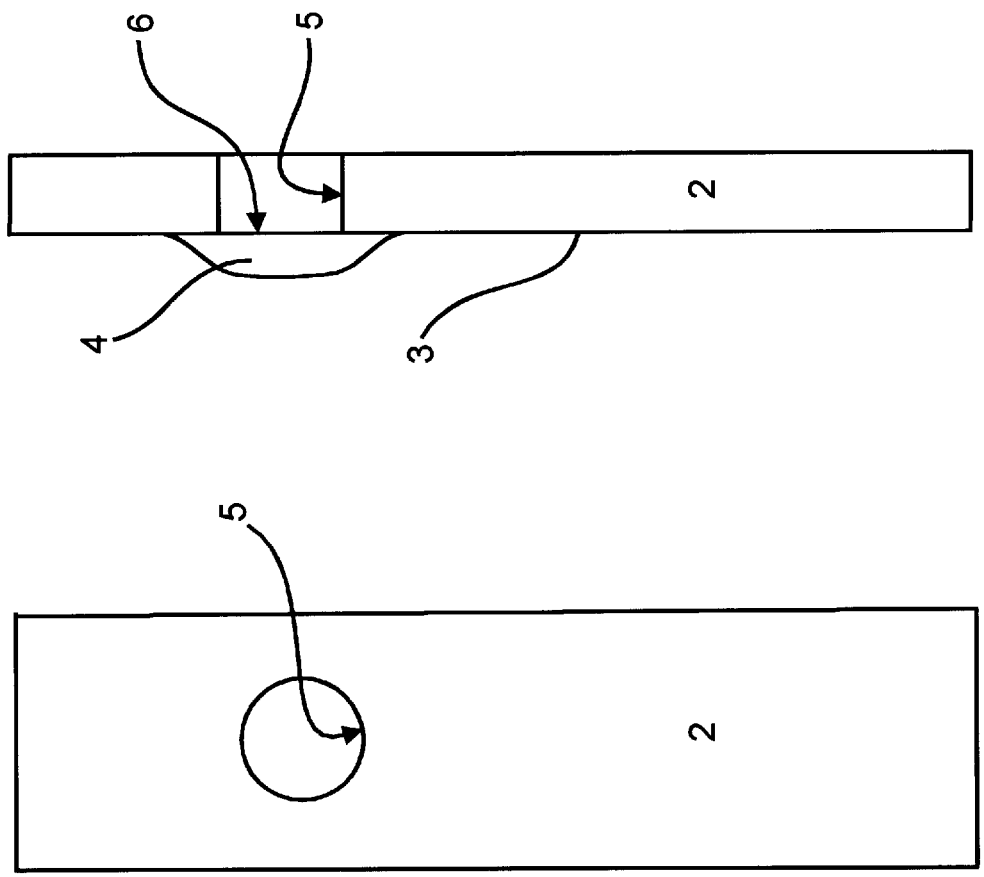
FIG. 1 is a diagram illustrating an example of a test strip used by a method and apparatus according to the present invention.
Figure 2:
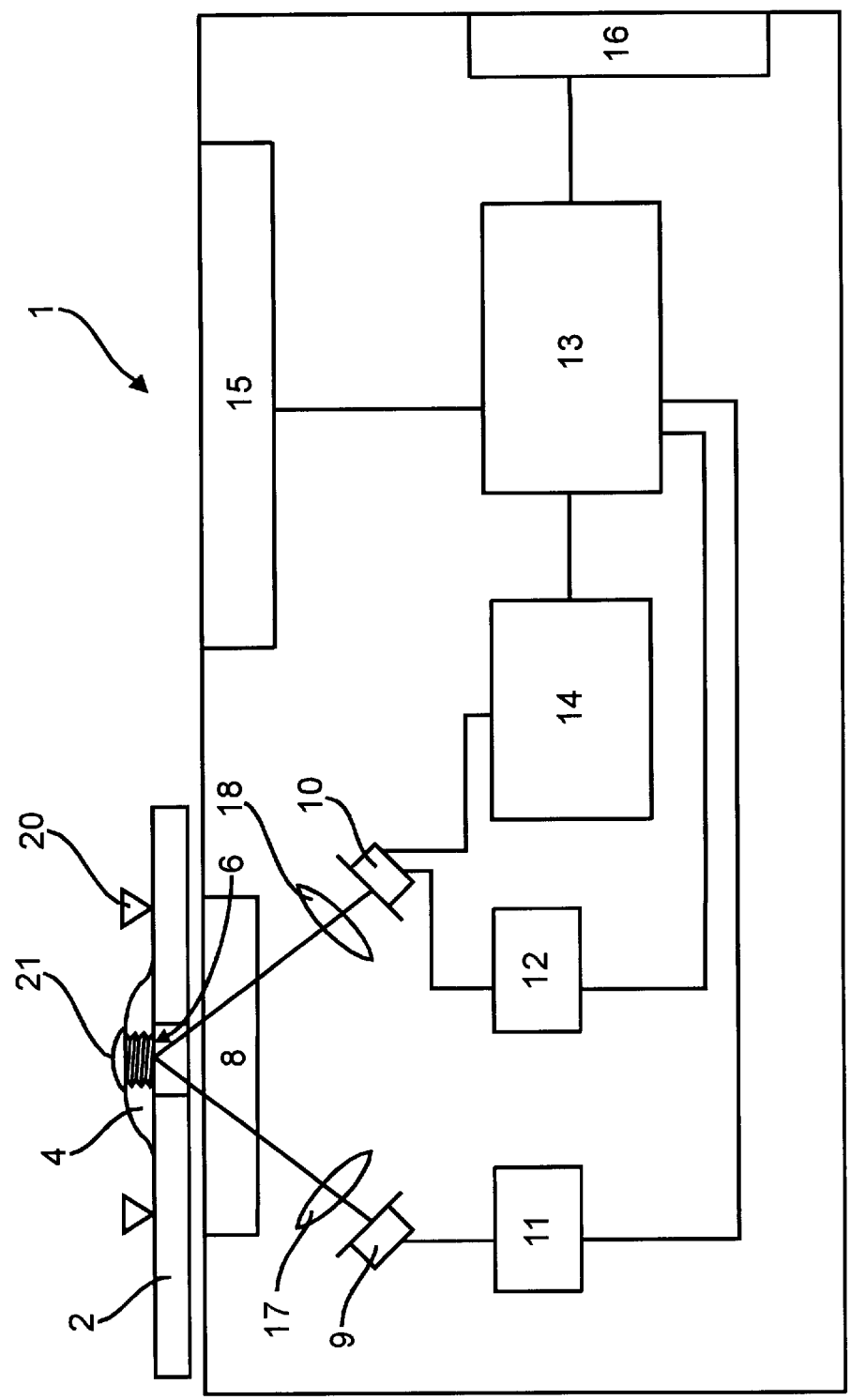
FIG. 2 is a functional block diagram of an exemplary embodiment of an apparatus according to the present invention for performing the method of the present invention.

FIGS. 1 and 2 show the test strip 2 used in an embodiment of a method according to the present invention, and an embodiment of an apparatus 1 for performing the method according to the present invention. The test strip 2 involves a reagent entering into chemical reaction with the sample component to be determined. In the embodiment shown in FIGS. 1 and 2, the apparatus 1 is a blood glucose measuring device, which constitutes a blood glucose measurement system together with the known test strip 2, the latter is a known no-wipe type test strip. FIG. 1 shows different views of the test strip 2, from left to right: from the top, bottom and side. As is apparent from FIG. 1, on the top side 3 of the test strip 2 there is a 4 reagent matrix, also called a test pad, which contains the reagent entering into chemical reaction with the sample to be measured. The reagent matrix 4 is made of a textile or foil in a known manner. Below the reagent matrix 4 there is a hole 5 in the test strip 2. The result of the reaction is measured by apparatus 1 through the hole 5 on the lower surface 6 of the reagent matrix 4.

FIG. 2 shows the principal construction of the blood glucose measurement apparatus 1. The test strip 2 is positioned on an external surface of the apparatus, preferably on the top, and fastened temporarily by a known fastening mechanism 20 to the measuring window 8 of the apparatus 1. The test strip 2 is positioned in a manner so that the hole 5 substantially coincides with the measuring section of the measuring window S. The apparatus 1 is composed of a light source 9, such as a LED, with well defined properties, and providing substantially monochrome light. The light of the light source 9 is imaged by the beam forming optics 17 onto the lower surface 6 of the reagent matrix 4. The light reflected from the lower surface 6, or a fraction thereof, is measured by the detector 10, in the present case, through the imaging optics 18.

The values measured by the detector 10 are forwarded via the A/D converter 14 to the microprocessor 13. The glucose content calculated on the basis of the values measured by the detector 10 is displayed on the display 15 and/or transmitted to other data processing units via the interface 16. In practice, the 13 microprocessor controls the power supplies 11 and 12, where the latter are supplying power to the light source 9 and the detector 10, respectively. This latter function of the microprocessor 13 is not necessary to the present invention, but, in order to minimize the power consumption, it is advantageous to switch on the light source 9 and the detector 10 during the actual measurement only and, therefore, the power supplies 11 and 12 are switched on and off by the microprocessor 13.

The blood glucose measuring apparatus 1, according to the present invention, is used in the following manner: Before starting the measurement, the user—typically a diabetic measuring his/her own blood sample—places a test strip 2 on the apparatus 1 and switches on the apparatus.

Optionally, the test strip 2 may be placed on the apparatus 1, also after switching on, if the microprocessor of the apparatus also includes an algorithm which is capable of distinguishing between changes in the reflection caused by the placement of the test strip 2 from the changes in the reflection caused by the actual measurement. The latter will be explained below in greater detail together with respect to and embodiment of the method according to the present invention.

After switching on the apparatus 1, the detector 10 measures continuously or at intervals or by sampling in time points the R reflection of the lower surface 6 of the reagent matrix 4. By continuous or substantially continuous measurement it is meant that the sampling frequency of the reflection measurement is as large as possible, i.e., made with at least as large a frequency with which the microprocessor 13 or any other controlling and analyzing unit is capable of processing the reflection data. If the algorithm of the invention is embodied in analog circuitry, then the reflection measurement may be effectively continuous.

Returning to the value of the reflection R measured on the lower surface 6 of the test strip 2, the reflection R will obviously remain constant, until the user places a blood sample—typically a blood drop 21 of capillary blood—on the top surface of the reagent matrix 4, opposite to the lower surface 6. Certain components of the blood drop, especially the blood plasma containing the blood glucose, will penetrate the reagent matrix 4 by wicking action, and will reach the other side, the lower surface 6. As a result, the R reflection measured on the lower surface 6 will change, and this change is detected by the detector 10.

The signals from the detector 10 are digitized by the A/D converter 14, and forwarded to the microprocessor 13. The microprocessor 13 is programmed to perform an embodiment of the method according to the invention, which is described in greater detail below. The microprocessor 13 automatically controls the power supply 11 of the light source 9, at the rate of the sampling frequency. At the same time, the microprocessor 13 automatically generates the R(t) function, or more precisely, the $R(T_i)$ points of the R(t) function, and the functions $R_{corr}(t)$ and F(t) calculated from the R(t) function. In another possible embodiment of the present invention, during the calculation of the $R_{corr}(t)$ and F(t) functions, the values of the L(t) and C(t) functions are not calculated for the individual $T_o$, $T_i$, $T_{min}$ and $T_m$ and other time points, but the function values are stored in a storage unit (not shown) in a tabular form, and the required function values are retrieved from the table as needed.

The R reflection measured by the detector 10 is a result of several different processes, which may coincide at least partly, or may proceed separately, in time. The first process is the wetting by the fluid, which is primarily a physical process, and the change in the reflection is caused by the change of the refractive index and the surface structure of the reagent matrix 4. This process involves a relatively fast decrease of the reflection R. The next process influencing the reflection is the chemical process actually used to determine the glucose content in the blood. During this reaction the glucose content of the blood will react with a reagent, e.g., the glucose-oxidase enzyme, and further with the water and oxygen, and the resulting substance, the hydrogen peroxide, will cause a further color reaction. The latter results in a characteristic coloring, typically blue, on the lower surface 6 of the reagent matrix 4. This blue coloring will appear as a further decrease of the reflection R, because the light of the LED, which is radiating in the infrared range, will be reflected less towards the detector 10. This change in coloring is followed by other processes, which are no longer relevant to the blood glucose measurement, and may actually negatively influence the result of the measurement. Therefore, the reflection R serving as the basis of the glucose content determination should be measured after the end of the second process, but before the start of the following processes that may disturb the results.

According to the present invention, the $T_m$ measurement time of the reflection measurement used for determining the glucose content may be selected in the manner described below. As noted above, the detector 10 of the apparatus 1 is measuring continuously in discrete sampling time points $T_i$; the reflection R. Continuously monitoring and analyzing the value of the reflection R, it is possible to determine approximately the time point $T_o$ when the fluid containing the blood glucose wicked through the reagent matrix 4 to the lower surface 6, causes this wetting which produces a sudden drop in the reflection R. This sudden drop may be detected easily, most simply by determining when the reflection R falls below a threshold value. This time point is regarded in the following as the value $T_o=0$. Other methods to determine $T_0$ are also suitable, e.g. when the difference $dR=(R_{n+1}-R_n)$ or the ratio dR/dt reaches a predetermined threshold, it may also signal the reaching of the time point $T_o$. Alternatively, the wetting may be detected by an electrical method, such as by a capacitance measurement.

From the time point $T_0$, the corrected reflection function $R_{corr}(t)=R(t)+L(t)$ is generated, i.e., its actual values in the discrete time points. The L(t) function is a predetermined function, which may be determined experimentally, or it may be used in the form of an L(t)=At+B, a linear approximation. The function L(t) also has a reflection dimension, but it is not possible to attribute a direct physical meaning to L(t). Methods to define the function L(t) will be explained in greater detail below.

The value of the function $R_{corr}(t)$ is also monitored continuously, and the true extreme $ext(R_{corr})$ is sought. Experience shows that the first true extreme of $R_{corr}$ will be a minimum, which is reached in the time point $T_{min}>T_o$. As long as the function $R_{corr}(t)$ is decreasing, the extreme value, i.e., the minimum, will always be the last $R_{corr}(t)$ value. The sought value is the first true extreme. i.e., the first $min(R_{corr})$ value for which it will be first true that $$min(R_{corr})=R_{corr}(T_{min})<R_{corr}(T_i), \text{ if } T_i>T_{min}.$$

As soon as this first true extreme $min(R_{corr})$ is found, the function $F(t)=(R_{corr}(t)-min(R_{corr})$ is also defined and generated. Obviously, from this time on, F(t) will be growing at least on a finite interval, because at the time point $T_{min}$ the function $R_{corr}(t)$ has a true local minimum. It is understood that the value of the reflection R at the time point $T_{min}$, actually through value $R_{corr}(T_{min})$ of the corrected reflection function $R_{corr}$, can be determined exactly, though the exact determination of the time point $T_{min}$ is not very important in the present invention. During the process, a relatively low sampling frequency can be applied, because in the proximity of the minimum $min(R_{corr})$ the function $R_{corr}(t)$ will be changing relatively slowly, and therefore even a value calculated from interpolation with a second-order polynomial will provide sufficiently exact results.

The measurements and the practical curves show that the sampling frequency should be adjusted to the processes around the time point $T_{min}$.

The interpolation above may be performed in the following manner: If it is detected in a certain time point $T_k$ that $R_{corr}(T_k)>R_{corr}(T_{k-1})$ then the value of the function $R_{corr}(t)$ is approximated by a second order polynomial $R_{corr}^*(t)$ laid through the points $T_{k-2}$, $R_{corr}(T_{k-2})$; $T_{k-1}$, $R_{corr}(T_{k-1})$; and $T_k$, $R_{corr}(T_k)$, or through further suitable points, preferably the closest neighboring points. Higher order approximations are also possible. After calculating the approximated minimum value $ext(R_{corr}^*)$, further on this value will be regarded as the true minimum value $ext(R_{corr})$ of the function $R_{corr}(t)$.

In the following, the function $F(t) = R_{corr}(t) - ext(R_{corr})$ is compared with the function $C(t)$, and the measurement time $T_m$ for measuring the reflection R which will serve as the basis for determining the glucose content is selected as the first time point T, in which the value of the function $F(t)$ reaches or surpasses the value of the function $C(t)$. In other words, $T_m$ is defined as the time point $T_m$ when it will be first true for $t=T_m$ that $F(T_m)-C(T_m) \geq 0$.

For even more precise measurements, the $F(t)-C(t)=0$ exact relation is sought, and for this purpose the function $F(t)$ is approximated with the interpolation $F^*(t)$, which may be a polynomial of a suitable order. From the relation $F^*(T_m^*)=C(T_m^*)$ the value of $T_m^*$ may be calculated exactly, and this interpolated time point $T_m^*$ approximates the sought time point $T_m$ with a high accuracy. Of course, the sought reflection value $R(T_m)$ is also calculated with interpolation from the reflection values $R(T_{j-i})$, ..., $R(T_{j-1})$, $R(T_j)$ measured in the time points $T_{j-i}$, ..., $T_{j-1}, T_j$, respectively, where the time point $T_m$ is in the time interval $T_{j-i}-T_j$.

It depends upon the design of the system and may be determined by one skilled in the art, whether the sampling frequency should be higher and the interpolation calculations be kept simpler, or whether the accuracy of the measurement should be improved by more sophisticated interpolating but the sampling frequency should be kept low. The $C(t)$ function may be also be determined experimentally, but in practice the approximation $C(t)=C$ proved to work well, i.e., $C(t)$ is a constant function. The value of C could be around 0.001–0.05.

As an example, using certain test strips, experiments were performed with samples of test liquid or blood using the above outlined method according to the present invention. The test strips used in the experiments were manufactured by Hypoguard Ltd. of Woodbridge, Suffolk, and sold under the Supreme brand name.

Figure 3:
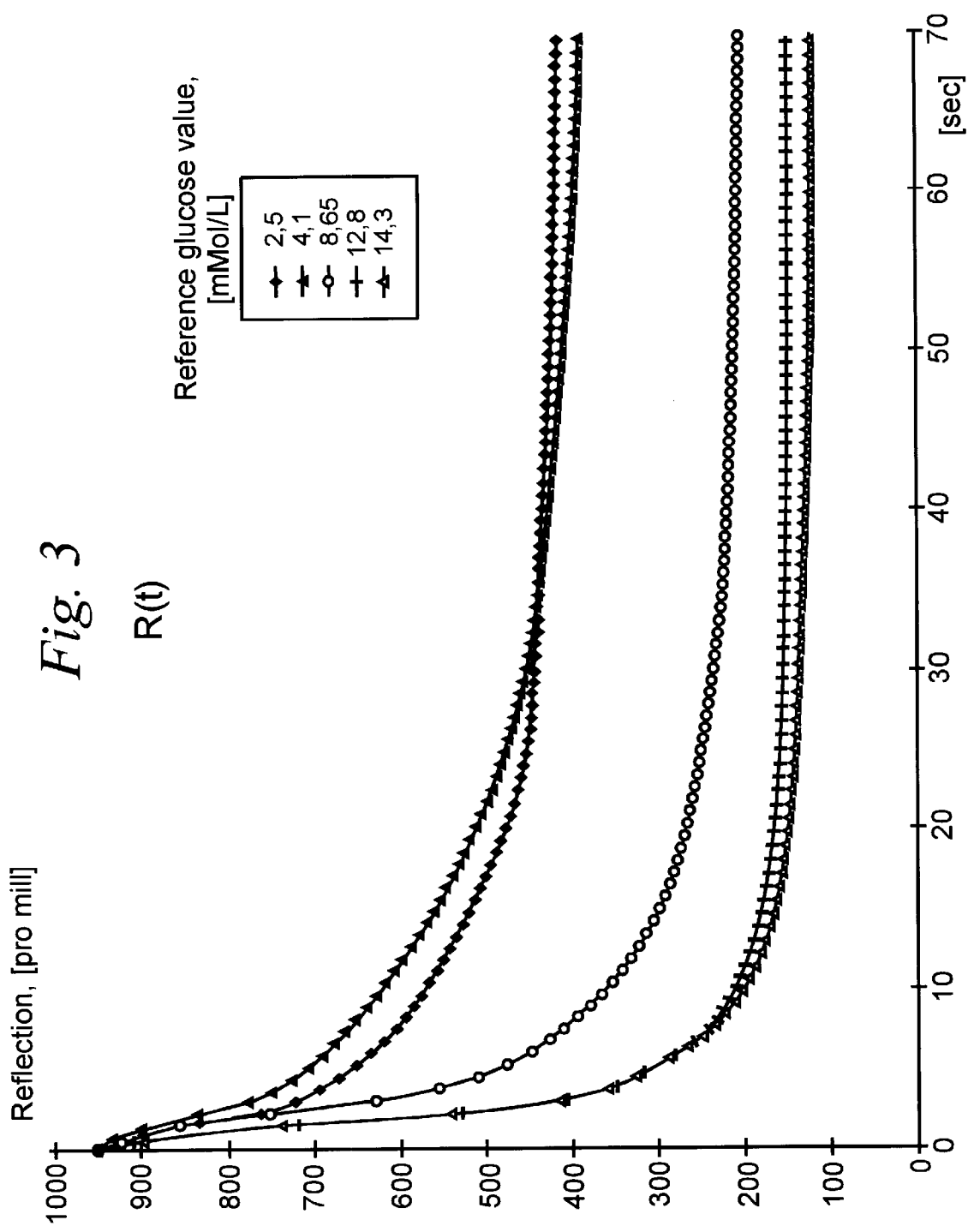
FIG. 3 is a graph that shows the reflection-time function of samples with different glucose levels, measured by the method according to the present invention.

The $L(t)$ function was taken into consideration using the following linear approximation: $L(t)=At$ in which $A=2.4$ pro mil/sec while the constant C value was 15 pro mil. FIG. 3 shows the reflection values measured on different test strips. It can be seen that, in samples with high glucose content, the reflection falls quicker because the color reaction also contributes more to the reduction in the reflection. The fact that the two processes are separated in time from each other can be clearly seen in FIG. 4. In this latter curve, the standard deviation of the R values of the test strips is compared to the reflection curves measured according to FIG. 3. In the measurements, sample solutions of 1 to 30 mMol/l glucose concentration were used (only a few characteristic values of the entire measurement series are shown in the figures).

It was presumed that the standard deviation is probably higher in the those parts of the reaction where the reaction rate is higher. Indeed, it can be clearly recognized that the maximum values of the two processes (wetting and color reaction) are separated from each other in time. It is also clear that the change in reflection caused by the wetting process decays very quickly, but the upward going section of the change in reflection attributable to the color reaction already suppresses this decay. The sought process is the color reaction, which should be completed before measuring the glucose content. It is evident that while the color reaction is in progress, the measurement made at that time would cause a high standard deviation. At the same time, after the end of the color reaction, it is advisable to measure as soon as possible, before any further disturbing processes would decrease the correlation between reflection and glucose content. Carrying out the measurement as soon as possible is also desirable from the viewpoint of the user comfort.

Figure 4:
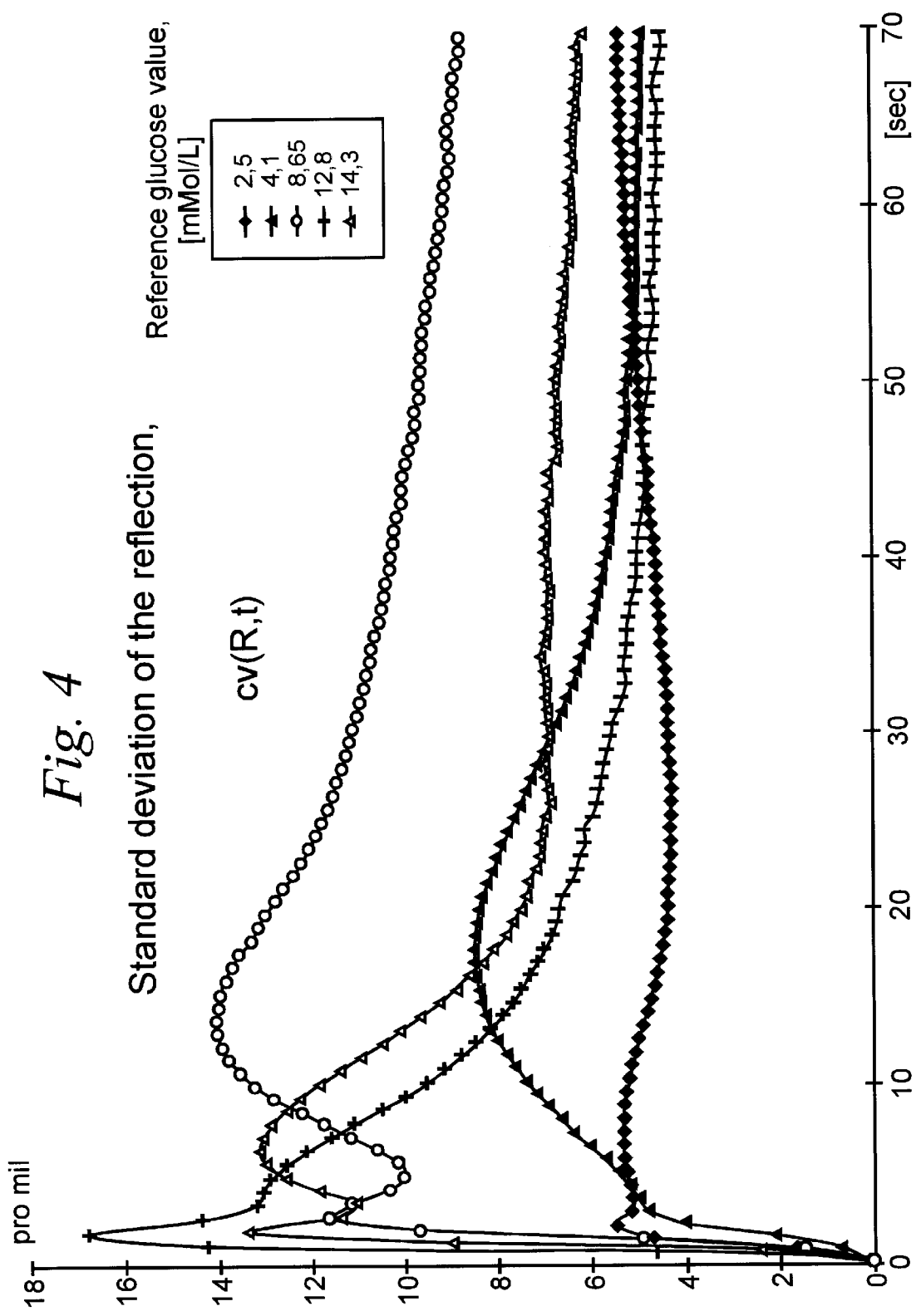
FIG. 4 is a graph that shows the standard deviation of several curves measured identically to those of FIG. 3.

In FIG. 4, it can be seen that the maximum values of the relative standard deviation function cv (R,t) are substantially in the same time interval, and it was determined from other measurements that those sections of the R(t) reaction curve that coincide with the highest reaction rate of the color reaction have practically the same or similar slope. Therefore, the problem to be solved can be reformulated in the sense that in order to find the maximum of the color reaction, the point should be found on the reflection curve where the curve has a predetermined slope. This may be found in a very simple way, according to the present invention, that is, a function with the a predetermined slope value must be added to the reflection curve and a true extreme value of the so defined function must be found.

Figure 5:
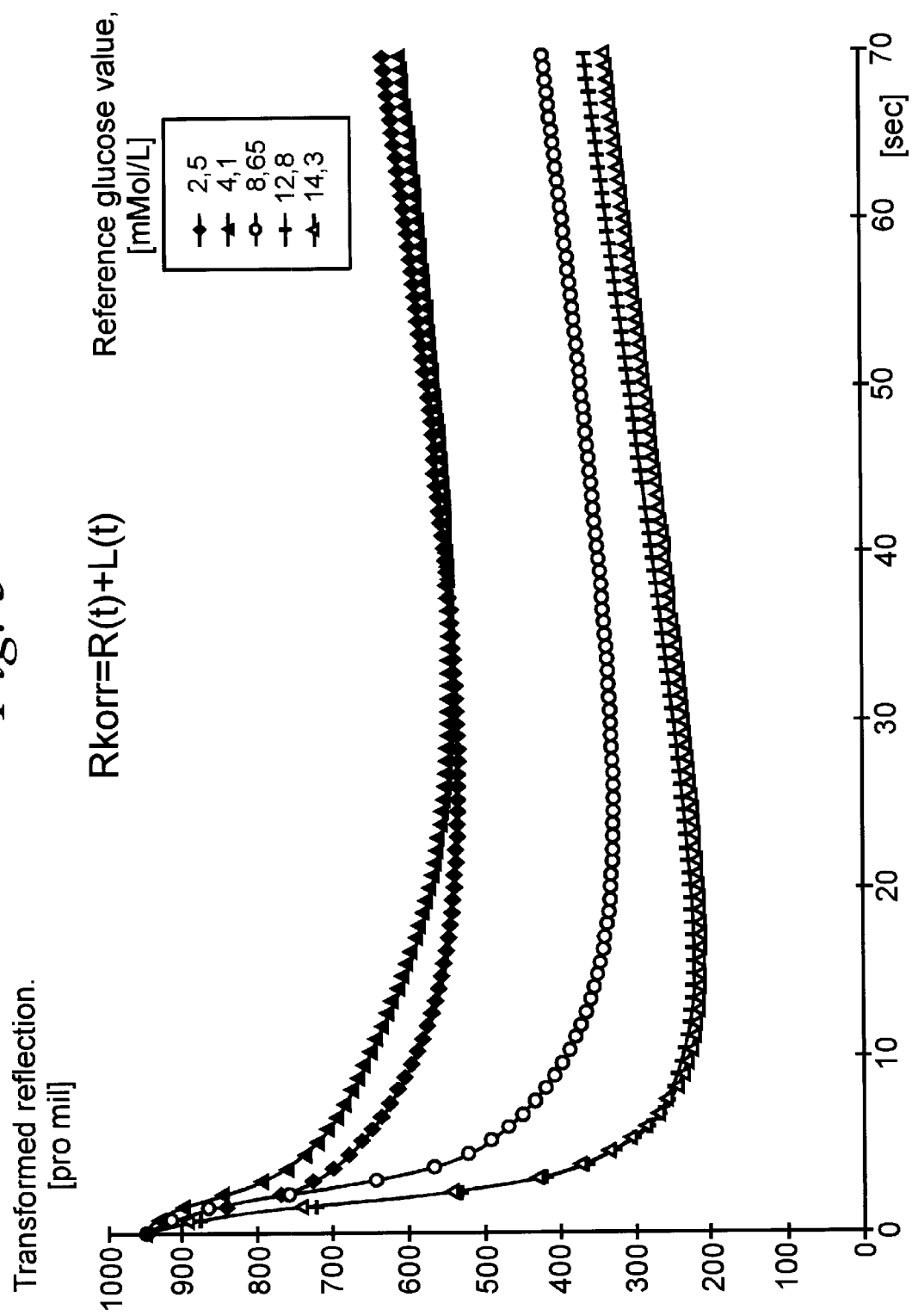
FIG. 5 is a graph that shows the $R_{corr}=(R(t)+L(t))$ transformation of the curves of FIG. 3.
Figure 6:
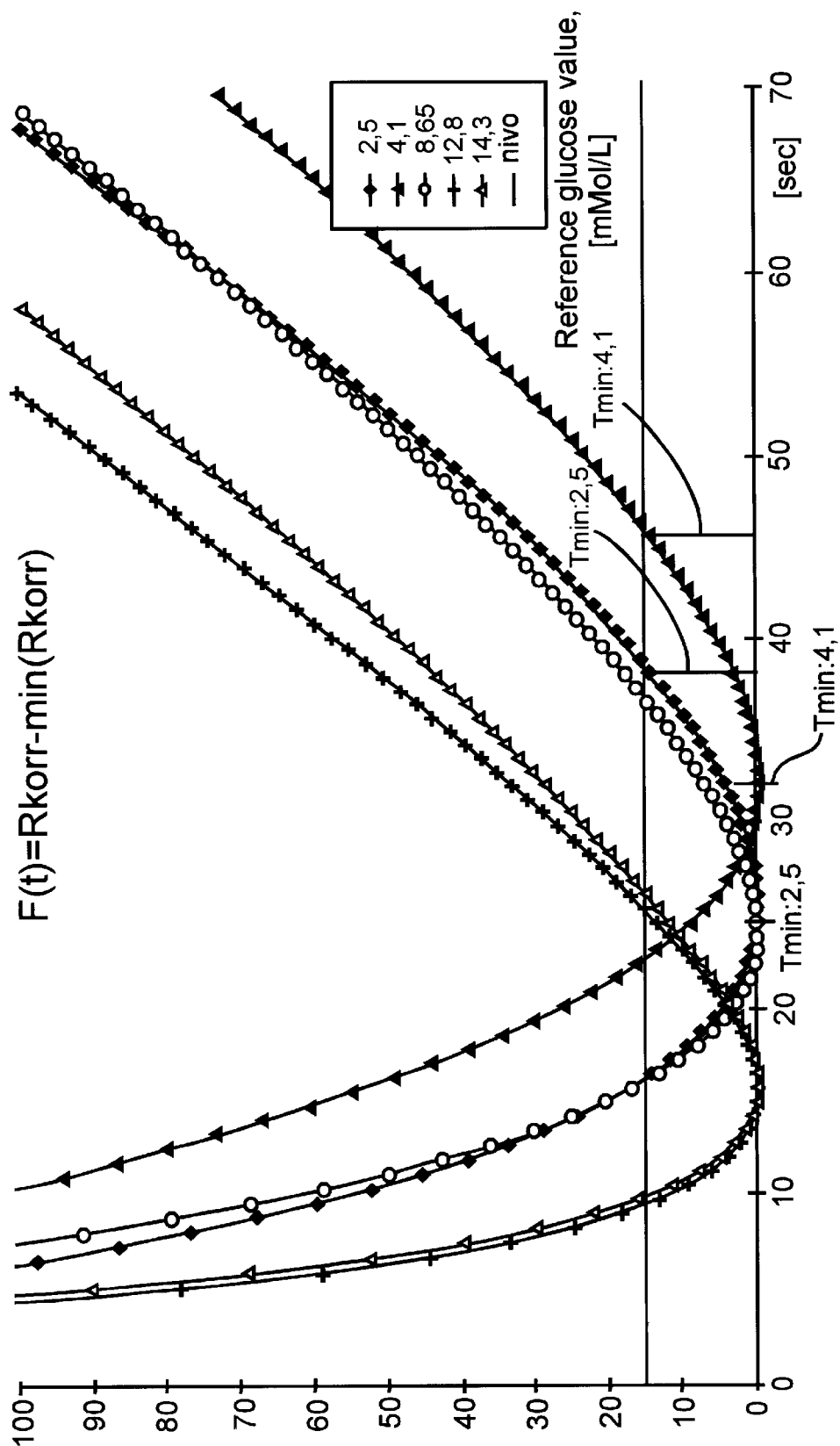
FIG. 6 is a graph that shows the $F(t)=R_{corr}-min(R_{corr})$ transformation of the curves of FIG. 5.

In the used color reaction, the reflection will be reduced. Therefore, the sought extreme value will be a minimum. This is illustrated by FIG. 5, which presents the values of the corrected reflection function $R_{corr}=R(t)+L(t)$ deduced from the reflection values of FIG. 3. The curves obtained after determining the minimum and the transformation of subtracting the minimum value are shown in FIG. 6, which shows the actual values of the functions $F(t)=R_{corr}+min$ $(R_{corr})$. In the lower part of FIG. 6, the constant function $C(t)=C$ is shown, marked in the legend by a "nivo" label.

As can be seen from the figures, with the test strips applied in this measurement series, it was possible to achieve, by the appropriate selection of the function $L(t)$, that the measuring system programmed according to the invention will measure samples of high glucose content sooner, those of lower glucose content later. It can be seen in FIG. 6 that, for example, with the sample of 2.5 mMol/l concentration, the time of $T_{min}$ will fall approximately toward 24 seconds and the $T_m$ time to about 38 seconds. In the case of a sample of mMol/l concentration, $T_{min}$ will be near 33 seconds while $T_m$ will approximate 46 seconds. Comparing this to FIG. 3, it can be seen that the measurement of the 4.1 mMol/l sample could be shifted to a time when the developed color will characterize its glucose content more reliably.

Figure 7:
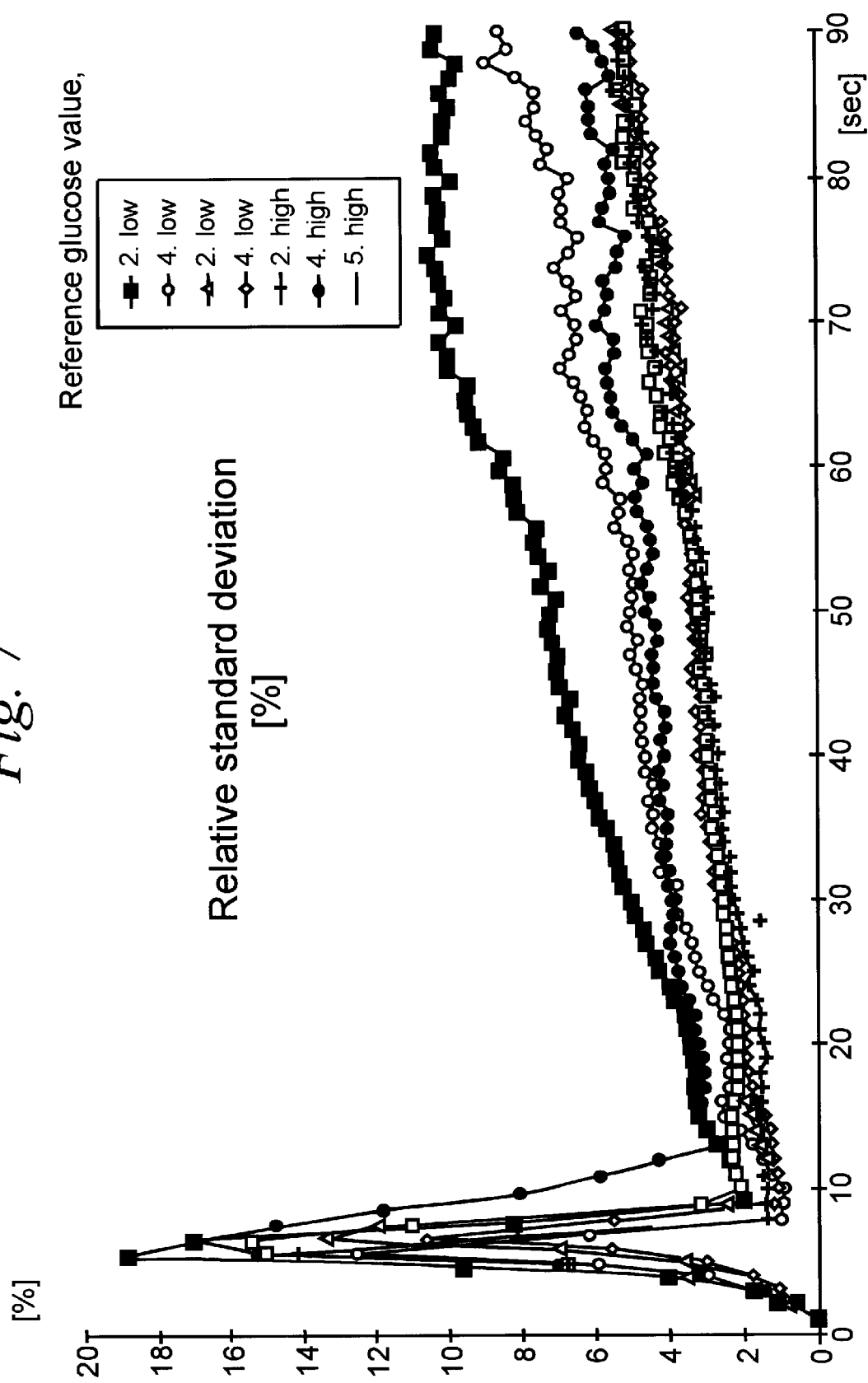
FIG. 7 is a graph that shows the relative standard deviation of curves measured with the parameters of FIG. 3.

FIG. 7 illustrates the standard deviation of test strips measuring samples with high and low glucose concentration. The average standard deviation is a few per cent in samples of low sugar content. This result is not inferior to the standard deviation of other known blood glucose determination methods.

Figure 8:
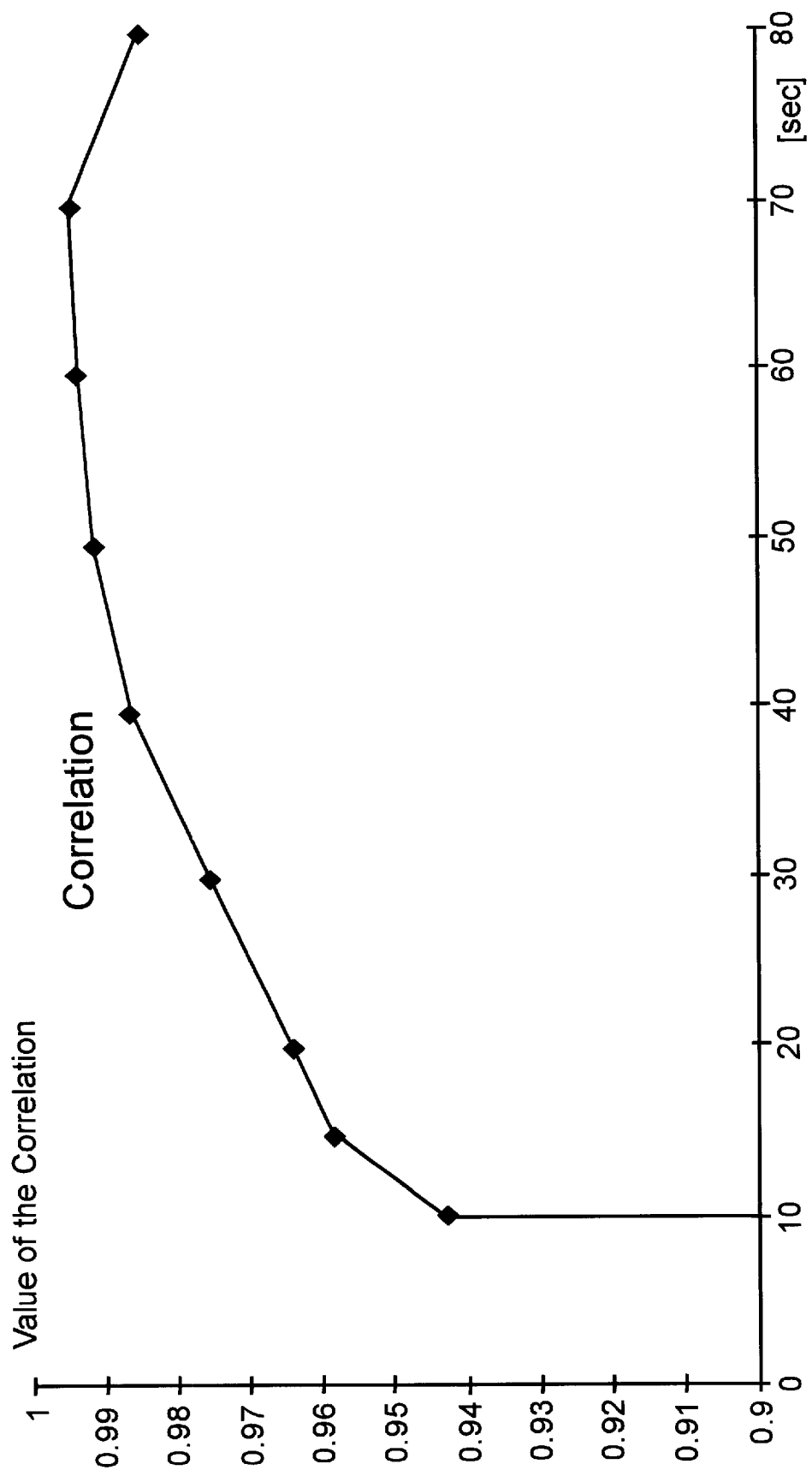
FIG. 8 is a graph that shows the correlation curve.

The correlation curve presented in FIG. 8 shows the correlation between the $T_m$ times determined on samples with various concentrations and the concentrations calculated from the reflections R at the times $T_m$. The curve mirrors the results measured and calibrated on a sample series comprising 26 different concentrations, with 20 sample groups with identical concentrations within each concentration range. It is clearly visible that the correlation is very high with short measurement times, e.g., it already reaches 0.96 at 20 seconds. The measurements have also shown that the combined error of the optical measurement and the method according to the invention is less than the error introduced into the measurement by the chemical reaction.

FIG. 9 shows the F(t) function measured on another type of test strip. It can be seen that, in this test strip, the samples with lower glucose content reach first the threshold determined by the constant C, that is, the method measures these sooner, while the samples of higher glucose content are measured later, after the completion of the reaction. In this case, for example, at the sample of 2.7 mMol/l concentration, the time of $T_{min}$ falls in the region of about 7 seconds, and the $T_m$ time to about 17 seconds. In the case of the sample with 8.55 mMol/l concentration, $T_{min}$ falls to about 11 seconds and $T_m$ to about 39 seconds.

The parameters of the L(t) and C(t) functions of the measurements above were determined as follows. In order to simplify the measurement and the programming, certain restricting presumptions were introduced:

1. The function L(t) is linear, at t=0 it is 0 (this choice is arbitrary and it does not affect the result). Thus, the determination of the L(t) function was simplified substantially to finding a slope value [ L(t)=At+B, but B=0].

2. The function C(t) is constant in time [ C(t)=C].

We formulated the problem so that the goal is to determine those "A" and "B" parameters in which the quantity of blood glucose can be determined with the least standard deviation as compared to the reference measurements. For reference measurements various blood glucose measuring instruments using known methods were applied, these were the reference devices. The measurement results obtained with the reference instruments were averaged and this average value was considered is the exact glucose value.

For determining the parameters 1192 reflection-time values were measured, on the Hypoguard Supreme test strips. In one time series, we used the most frequent sampling that was permitted by an experimental model of the apparatus according to the invention. In this manner, a measured value was generated in every 0.75 seconds. Each measured time series contained 100 samplings, so the duration of the individual measurement periods was 100*0.75=75 sec. The 119,200 data points obtained in this way were processed using an appropriate spreadsheet program by methods known to those of skill in the art. It should be noted that, in a given case, in order to optimize a non-linear L(t) function scientifically correctly, a substantially larger number of measurements is recommended. The glucose content of the samples used in the measurements were in the range 1 mMol/l to 30 mMol/l.

In the first step, the value of the C constant was chosen to be 15 pro mil, where 1000 pro mil is defined as the reflection value measured on a dry strip without a sample present. After this, with different A parameters (ranging from 0 to 5 in steps of 1), we calculated the $T_m$ measurement time determined by the formula F(t)=R(t)+L(t)=min[R(t)+L(t)]=C according to the invention. We also determined the $R(T_m)$ reflection values at the measurement time $T_m$, calculating $R(T_m)$ by means of interpolation from the reflection values $R_i(T_i)$ measured in time points $T_i$ around the time $T_m$. The $R(T_m)$ reflection values so obtained with the help of the F transformed reflection were converted into mMol/l values using a conversion table This conversion table was calibrated in a manner similar to the calibration of the conversion tables of the conventional methods. The correlation of the mMol/l values thus obtained were tested against the reference values.

As a result of the first step, we continued to refine the A parameter value from 2 to 3 pro mil, in steps of 0.1. The best correlation was obtained at 2.4 pro mil/sec. After this followed the refining of the C parameter value applying again correlation calculation. with a known recursive approximation algorithm.

Finally, as a result of the calculations, the local maximum of the correlation was obtained at A=2.4 pro mil/sec and C=15 pro mil. The value of the correlation found was 0.96, which is not inferior to the correlation of prior known methods, and further refinement is unnecessary because the chemical processes of the measurement, in particular the standard deviation of the result of the color reaction, already suppresses the standard deviation caused by the optical system and the evaluation algorithm. Another characteristic value is that at A=2 pro mil/sec, the correlation is a mere 0.79, while at A=3 pro mil/sec it is already 0.95.

In the above described measurements using the method according to the present invention, we measured various test strips using the above described A and C values. We found that the method provided good results even with the test strip for which the value of the A and C parameters had not been optimized. However, the method according to the present invention generally provides the best results if the parameters of the L(t) and C(t) functions have been calibrated to the test strip to be measured.

The present invention is not confined to the detailed embodiments described above, but, as persons of ordinary skill in the art will readily appreciate, variations may be made without departuring from the scope and spirit of the present invention. For example, there is nothing to prevent the method according to the invention, being used in a method using the same principle, but determining glucose, protein or some other component, from a urine sample instead of blood. The method according to the invention can also be used in devices where the wetting of the test strip is not detected automatically or not detected by an optical method, but it is determined by the user or, optionally, it is measured by some other method, e.g. by measuring electric resistance or capacitance. The L(t) and C(t) functions described above are presented as a suggested example, but other functions, like higher order polynomials or various other analytic functions are equally applicable. For example, C(t) may be chosen in the form C(t)=D−Gt, which will result in the determination of the measurement time $T_m$ not later than $T_{min}$+D/G. This way, it is ensured that the measurement will have a definite end under any circumstances.

The true scope and spirit of the present invention is defined by the appended claims, interpreted in light of the foregoing.

I claim:

1. An apparatus for determining a chemical component from a sample of matter, the apparatus comprising:

a sample holder for accommodating a test strip, the test strip being configured to receive the sample on one side of the test strip, the test strip including a reagent, the reagent being configured to cause a color reaction, directly or through an intermediate reaction, with the chemical component, and the test strip being further configured such that components of the sample penetrate the test strip and start the color reaction at an opposing side of the test strip;

a light source for illuminating the sample placed into the sample holder;

a measuring circuit for measuring the intensity of the light reflected from the sample and generating an output signal corresponding to the intensity of the light;

a controller and analyzer circuit for receiving the output signal from the measuring circuit, where the controller and analyzer circuit is configured to determine the chemical component of the sample by:

illuminating the sample and measuring a reflection R from the test strip and recording a reflection function R(t), detecting a wetting through of the sample, determining a starting time $T_0$, where the starting time $T_0$ is not earlier than the time of detection of wetting through of the sample, generating from the starting time $T_0$, a function R(t)+L(t), where L(t) is a predetermined function that is independent of the measured reflection, monitoring and storing an extreme value ext[R(t)+l(T)] of the R(t)+L(t) function, generating a function R(t)+L(t)−ext[R(t)+L(t)] from the time of reaching at least one value for extreme value ext[R(t)+L(t)], where the R(t)+L(t)−ext[R(t)+L(t)] function reaches a predetermined C(t) value, determining a $T_m$ measuring time, C(t) being a predetermined function independent of the measured reflection, and determining from the R reflection value measured at the $T_m$ measuring time an amount of the chemical component in the sample.

2. The apparatus of claim 1, where the controller and analyzer circuit is further configured to measure the reflection R at one of discrete time intervals and substantially continuously.

3. The apparatus of claim 1, where the controller and analyzer circuit is further configured to store a minimum value min[R(t)+L(t)] as the extreme value ext[R(t)+L(t)] of the R(t)+L(t) function.

4. The apparatus of claim 1, where the controller and analyzer circuit is further configured to generate the function R(t)+L(t)−ext[R(t)+L(t)] upon reaching a definite (true) value for the extreme value ext[R(t)+L(t)].

5. The apparatus of claim 1, where the sample of matter farther comprises a blood sample and the chemical component further comprises glucose.

6. The apparatus of claim 1, the apparatus further comprising a storage circuit configured to store values for one of the L(t) and C(t) functions in tabular form, the storage circuit being coupled to the controller and analyzer circuit.

7. The apparatus of claim 1, where the controller and analyzer circuit further comprises a microprocessor.

8. An apparatus for determining a chemical component from a sample of matter, the apparatus comprising:

means for accommodating a test strip, the test strip being configured to receive the sample on a reagent, the reagent being positioned on one side of the test strip, the reagent being configured to cause a color reaction, directly or through an intermediate reaction, with the chemical component to be measured, and the test strip being configured so that components of the sample penetrate the test strip and start the color reaction at the other side of the test strip; and means for measuring a content amount of a component in the sample through optical reflection measurement of the resulting color reaction by illuminating the sample and measuring at discrete time intervals or substantially continuously a reflection R on the test strip and recording a function R(t);

means for detecting a wetting through of the sample in order to determine a starting time $T_0$, where $T_0$ is not earlier than the time of detection of wetting through;

means for generating from the $T_0$ starting time a function R(t)+L(t), where L(t) is a predetermined function that is independent of the measured reflection;

means for monitoring and storing an extreme value ext[R(t) +L(t)] of the R(t)+L(t) function;

means for generating a function R(t)+L(t)−ext[R(t)+L(t)] from a time of reaching at least one extreme value ext[R(t)+L(t)];

means for determining a $T_m$ measuring time when the R(t)+L(t)−ext[R(t)+L(t)] function reaches a predetermined C(t) value; and means for determining the content of the chemical component in the sample by comparing the R reflection value measured at the $T_m$ measuring time to a predetermined calibrated measurement.

9. The apparatus of claim 8, where the means for generating a function R(t)+L(t)−ext[R(t)+L(t)] from a time of reaching at least one extreme value ext[R(t)+L(t)] further comprises means for generating the minimum value min[R(t)+L(t)] of the R(t)+L(t) function.

10. The apparatus of claim 8, where the sample further comprises a blood sample and the chemical component further comprises glucose.

11. The apparatus of claim 8, where L(t) further comprises a linear function with a predetermined slope, where L(t)=At+B, the variables A and B being constants.

12. The apparatus of claim 11, wherein B=0.

13. The apparatus of claim 8, wherein L(t) further comprises one of a second-order and a higher-order polynomial.

14. The apparatus of claim 8, where C(t) further comprises a constant function.

15. The apparatus of claim 8, where C(t) further comprises one of a first-order and a second-order polynomial.

16. The apparatus of claim 8, where the means for detecting the wetting through of the sample further comprises means for detecting the wetting through of the sample on the basis of one of: a predetermined amount of change in reflection; and a predetermined rate of change in reflection.

17. The apparatus of claim 8, wherein the means for detecting the wetting through of the sample further comprises means for detecting the wetting through of the sample on the basis of the reflection value R reaching a predetermined limit.

18. The apparatus of claim 8, where the step detecting the wetting through of the sample further comprises means for electrically detecting the wetting through of the sample on the basis of change in one of resistance and capacitance.

19. The apparatus of claim 8, where the sample further comprises one of full blood, blood plasma and serum.

20. The apparatus of claim 8, where the means for illuminating the sample further comprises means for illuminating the sample by applying illumination with an intensity substantially in the range of 0.01 to 1 mW and having a wavelength substantially in the range of 400 to 1550 nm.

21. A system for determining a chemical component from a sample of matter, the system comprising:

means for illuminating the sample and measuring a reflection R from a test strip and recording a reflection function R(t);

means for detecting a wetting through of the sample when the sample has been provided on the test strip;

means for determining a starting time $T_0$, where the starting time $T_0$ is not earlier than the time of detection of wetting through of the sample;

means for generating from $T_0$ starting time a function R(t)+L(t), where L(t) is a predetermined function that is independent of the measured reflection;

means for monitoring and storing an extreme value ext[R(t)+L(t)] of the R(t)+L(t) function;

means for generating a function R(t)+L(t)−ext[R(t)+L(t)] from the time of reaching at least one value for extreme value ext[R(t)+L(t)];

means for determining a $T_m$ measuring time when the $R(t)+L(t)-ext[R(t)+L(t)]$ function reaches a predetermined $C(t)$ value, $L(t)$ and $C(t)$ being predetermined functions independent of the measured reflection; and means for determining from the R reflection value measured at the $T_m$ measuring time an amount of the chemical component in the sample.

22. The system of claim 21, where the means for illuminating the sample and measuring a reflection R includes means for measuring the reflection R at one of discrete time intervals and substantially continuously.

23. The system of claim 21, where the means for monitoring and storing an extreme value $ext[R(t)+L(t)]$ of the $R(t)+L(t)$ function includes means for storing a minimum value $min[R(t)+L(t)]$ as the extreme value $ext[R(t)+L(t)]$ of the $R(t)+L(t)$ function.

24. The system of claim 21 where the means for generating a function $R(t)+L(t)-ext[R(t)+L(t)]$ from the time of reaching at least one value for extreme value $ext[R(t)+L(t)]$ further comprises means for generating the function $R(t)+L(t)-ext[R(t)-L(t)]$ upon reaching a definite (true) value for the extreme value $ext[R(t)+L(t)]$.

25. The system of claim 21, where the sample of matter further comprises a blood sample and the chemical component further comprises glucose.

* * * * *